(12) United States Patent
Capone et al.

(10) Patent No.: US 11,630,965 B2
(45) Date of Patent: Apr. 18, 2023

(54) IDENTIFICATION TAG READER SYSTEM

(71) Applicant: BAYER HEALTHCARE LLC, Whippany, NJ (US)

(72) Inventors: Christopher Capone, Pittsburgh, PA (US); Jaroslaw Wlodarczyk, Lower Burrell, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 22 days.

(21) Appl. No.: 17/226,639

(22) Filed: Apr. 9, 2021

(65) Prior Publication Data
US 2021/0232785 A1   Jul. 29, 2021

Related U.S. Application Data

(63) Continuation of application No. 16/479,986, filed as application No. PCT/US2018/019190 on Feb. 22, 2018, now Pat. No. 10,977,463.
(Continued)

(51) Int. Cl.
*G06K 7/10* (2006.01)
*A61M 5/145* (2006.01)
*G06K 7/14* (2006.01)

(52) U.S. Cl.
CPC ..... *G06K 7/10831* (2013.01); *A61M 5/14546* (2013.01); *G06K 7/1095* (2013.01); *G06K 7/1486* (2013.01); *A61M 2205/6072* (2013.01)

(58) Field of Classification Search
CPC ............ G06K 7/10831; G06K 7/1095; G06K 7/1486; A61M 5/14546;
(Continued)

(56) References Cited

U.S. PATENT DOCUMENTS 5,383,858 A   1/1995 Reilly et al.
6,322,535 B1  11/2001 Hitchins et al.
(Continued)

FOREIGN PATENT DOCUMENTS

EP   1563859 A1   8/2005
JP   5964231 B2   8/2016
(Continued)

OTHER PUBLICATIONS

"International Preliminary Report on Patentability from PCT Application No. PCT/US2018/019190", dated Sep. 12, 2019.
(Continued)

*Primary Examiner* — Seung H Lee
(74) *Attorney, Agent, or Firm* — Joseph L. Kent; James R. Stevenson; David Schramm

(57) ABSTRACT

A reader system for reading information on at least one identification tag associated with a syringe connected to a fluid injector has a detector and a background screen spaced apart from the detector such that at least one of the at least one identification tags is positioned in an optical path between the detector and the background screen when the syringe is connected to the fluid injector. The reader system further has an illumination system configured for illuminating at least a portion of the background screen. The detector is configured for detecting and decoding the at least one identification tag. Methods for reading information on at least one identification tag associated with a syringe are also described.

19 Claims, 13 Drawing Sheets

Related U.S. Application Data

(60) Provisional application No. 62/464,655, filed on Feb. 28, 2017.

(58) Field of Classification Search
CPC ........... A61M 2205/6072; A61M 2005/14573; A61M 2205/60; A61M 5/14566; A61M 5/16827

See application file for complete search history.

(56) References Cited

U.S. PATENT DOCUMENTS

| | | |
|---|---|---|
| 6,626,862 B1 | 9/2003 | Duchon et al. |
| 6,652,489 B2 | 11/2003 | Trocki et al. |
| 6,821,450 B2 | 11/2004 | Truninger et al. |
| 7,553,294 B2 | 6/2009 | Lazzaro et al. |
| 7,666,169 B2 | 2/2010 | Cowan et al. |
| 9,078,809 B2 | 7/2015 | Bochenko et al. |
| 9,173,995 B1 | 11/2015 | Tucker et al. |
| 9,199,033 B1 | 12/2015 | Cowan et al. |
| 9,474,857 B2 | 10/2016 | Riley et al. |
| 9,700,670 B2 | 7/2017 | Tucker et al. |
| 9,895,488 B2 | 2/2018 | Morton |
| 10,201,666 B2 | 2/2019 | Cowan et al. |
| 2004/0064101 A1 | 4/2004 | Kowan et al. |
| 2012/0215162 A1 | 8/2012 | Nielsen et al. |
| 2015/0374907 A1 * | 12/2015 | Morton ............. A61M 5/14546 604/111 |
| 2016/0296692 A1 | 10/2016 | Agris, III et al. |
| 2017/0119962 A1 | 5/2017 | Fazi, Jr. |
| 2017/0165427 A1 | 6/2017 | Uber, III et al. |

FOREIGN PATENT DOCUMENTS

| | | |
|---|---|---|
| WO | 2012155035 A1 | 11/2012 |
| WO | 2016045699 A1 | 3/2016 |

OTHER PUBLICATIONS

"Light Guide Techniques—Using LED Lamps", Avago Technologies, Dec. 11, 2006.

Van; Derlofske John F., "Computer modeling of LED light pipe systems for uniform display illumination", Lighting Research Center, Rensselaer Polytechnic Institute, 2001.

* cited by examiner

IDENTIFICATION TAG READER SYSTEM

CROSS-REFERENCE TO RELATED APPLICATIONS

This application is a Continuation of U.S. application Ser. No. 16/479,986, filed Jul. 23, 2019, which is a 371 national phase application under 35 U.S.C. § 371 of PCT International Application No. PCT/US2018/019190, filed Feb. 22, 2018, and claims priority to U.S. Provisional Application No. 62/464,655, filed Feb. 28, 2017, the disclosures of which are incorporated by reference herein in their entirety.

BACKGROUND OF THE DISCLOSURE

Field of the Disclosure

The present disclosure relates generally to a reader system configured for reading an identification tag. The reader system may be configured to assist reading an identification tag associated with a transparent or translucent surface. For example, the reader system may be associated with the fluid injector and configured to read an identification tag provided on a transparent or translucent surface of a syringe.

Description of Related Art

In the medical field, it is desirable to identify at least one property of a syringe and/or the fluid within the syringe. For example, information relating to the volume of the syringe and the type of fluid within the syringe may be useful in determining the volume of fluid that can be delivered, and the pressure and flow rate at which the fluid can be delivered using a fluid injector. In some examples, information relating to at least one property of the syringe and/or the fluid within the syringe can be encoded in the barcode that is provided on the syringe. Information encoded into the barcode can be scanned and sent to the fluid injector for controlling at least one example of the fluid delivery procedure.

Barcode readers, for example for reading standard barcodes and Quick Response (Q-R) codes, are used in numerous commercial applications. Typically, barcodes are printed or otherwise attached to an opaque surface of the barcoded product. As such, these barcodes are well defined against an opaque background and may be easily read by the barcode scanner. Visual contrast between the darkened regions and lighter background is particularly suitable for detecting the features of the barcode using the barcode scanner. However, differentiating between patterns of a barcode printed directly on a transparent or translucent material, such as when a barcode is provided on a transparent syringe, may not provide the contrast necessary for readily differentiating the features of the barcode.

While there exist several barcode reader systems, improved barcode reader systems and methods for reading barcodes from syringes and other barcoded products having a barcode applied on a transparent or a translucent surface continue to be in demand There is a need in the art for improving the visibility of the barcode on the syringe and other barcoded products having a barcode applied on a transparent or a translucent surface such that the barcode can be reliably and consistently read by the barcode reader system.

SUMMARY OF DISCLOSURE

In some examples, a reader system for reading information on at least one identification tag associated with a transparent surface, such as a syringe connected to a fluid injector, may have a detector and a background screen spaced apart from the detector such that at least one of the at least one identification tags is positioned in an optical path between the detector and the background screen, for example when the syringe is connected to the fluid injector. The reader system further may have an illumination system configured for illuminating at least a portion of the background screen. The detector may be configured for detecting the at least one identification tag on a backdrop defined by at least a portion of the background screen illuminated by the illumination system.

In some examples, the reader system may have a housing and a frame for enclosing the detector and the illumination system. The background screen may be spaced apart from the frame such that at least a portion of the syringe having the at least one identification tag is inserted in a space between the background screen and the frame when the syringe is connected to the fluid injector. The background screen may have a painted surface and/or a textured surface. The background screen may be curved. The background screen may be a light pipe. The detector may be positioned radially offset relative to the at least one identification tag such that the at least one identification tag is within a field of view of the detector. The detector may be positioned such that the at least one identification tag is outside a field of view of the detector and wherein one or more reflective elements are disposed between the detector and the at least one identification tag to define an optical path therebetween. The one or more reflective elements may be a mirror. The mirror may be flat, convex, or concave. The one or more reflective elements may be positioned in the optical path at about a 45° angle. The illumination system may have a plurality of light modules. The plurality of light modules may have uniform or non-uniform spacing therebetween. At least one of the plurality of light modules may be a light emitting diode. The detector may be a digital camera having a lens. The reader system may be provided inside a housing of the fluid injector and is operatively connected to a control mechanism of the fluid injector.

In other examples, a reader system may be provided for reading information on at least one identification tag associated with a syringe connected to a fluid injector. The reader system may have a detector, a background screen spaced apart from the detector such that at least a portion of the syringe having the at least one identification tag is inserted in a space between the background screen and the detector when the syringe is connected to the fluid injector. The reader system may further have one or more reflective elements disposed between the detector and the at least one identification tag to define an optical path therebetween. The reader system may further have an illumination system configured for illuminating at least a portion of the background screen. The detector may be configured for detecting the at least one identification tag against a backdrop defined by the background screen illuminated by the illumination system. The background screen may be a light pipe. The one or more reflective elements may be a mirror.

Various examples of the present disclosure may be further characterized by one or more of the following clauses:

Clause 1. A reader system for reading information on at least one identification tag associated with a syringe connected to a fluid injector, the reader system comprising: a detector; a background screen spaced apart from the detector such that at least one of the at least one identification tags is positioned in an optical path between the detector and the background screen when the syringe is connected to the fluid injector; and an illumination system configured for illuminating at least a portion of the background screen, wherein the detector is configured for detecting the at least one identification tag on a backdrop defined by at least a portion of the background screen illuminated by the illumination system.

Clause 2. The reader system of clause 1, further comprising a housing and a frame for enclosing the detector and the illumination system.

Clause 3. The reader system of clause 2, wherein the background screen is spaced apart from the frame such that at least a portion of the syringe having the at least one identification tag is insertable in a space between the background screen and the frame.

Clause 4. The reader system of any of clauses 1-3, wherein at least a portion of the background screen has a painted surface.

Clause 5. The reader system of any of clauses 1-4, wherein at least a portion of the background screen has a textured surface.

Clause 6. The reader system of any of clauses 1-5, wherein at least a portion of the background screen is curved.

Clause 7. The reader system of any of clauses 1-6, wherein at least a portion of the background screen is a light pipe.

Clause 8. The reader system of any of clauses 1-7, wherein the detector is positioned radially offset relative to the at least one identification tag such that the at least one identification tag is within a field of view of the detector.

Clause 9. The reader system of any of clauses 1-8, wherein the detector is positioned such that the at least one identification tag is outside a field of view of the detector and wherein one or more reflective elements are disposed between the detector and the at least one identification tag to define an optical path therebetween.

Clause 10. The reader system of clause 9, wherein the one or more reflective elements is a mirror.

Clause 11. The reader system of clause 10, wherein the mirror is flat, convex, or concave.

Clause 12. The reader system of clause 9, wherein the one or more reflective elements are positioned in the optical path at about a 45° angle.

Clause 13. The reader system of any of clauses 1-12, wherein the illumination system comprises a plurality of light modules.

Clause 14. The reader system of clause 13, wherein the plurality of light modules have uniform or non-uniform spacing therebetween.

Clause 15. The reader system of clause 13, wherein at least one of the plurality of light modules is a light emitting diode.

Clause 16. The reader system of any of clauses 1-15, wherein the detector comprises a digital camera having a lens.

Clause 17. The reader system of any of clauses 1-16, wherein the reader system is provided inside a housing of the fluid injector and is operatively connected to a control mechanism of the fluid injector.

Clause 18. A reader system for reading information on at least one identification tag associated with a syringe connected to a fluid injector, the reader system comprising: a detector; a background screen spaced apart from the detector such that at least a portion of the syringe having the at least one identification tag is insertable in a space between the background screen and the detector when the syringe is connected to the fluid injector; one or more reflective elements disposed between the detector and the at least one identification tag to define an optical path therebetween; and an illumination system configured for illuminating at least a portion of the background screen, wherein the detector is configured for detecting the at least one identification tag against a backdrop defined by the background screen illuminated by the illumination system.

Clause 19. The reader system of clause 18, wherein the background screen is a light pipe.

Clause 20. The reader system of clause 18 or 19, wherein the one or more reflective elements is a mirror.

Further details and advantages of the various examples described in detail herein will become clear upon reviewing the following detailed description in conjunction with the accompanying drawing figures.

BRIEF DESCRIPTION OF THE DRAWINGS

FIG. 14A illustrates an embodiment with no illumination of the background screen. FIG. 14B illustrates an embodiment where the light source is spaced radially away from the syringe surface adjacent to the detector. FIG. 14C illustrates an embodiment where the background screen is illuminated.

In FIGS. 1-14C, like characters refer to the same components and elements, as the case may be, unless otherwise stated.

DETAILED DESCRIPTION

Figure 1:
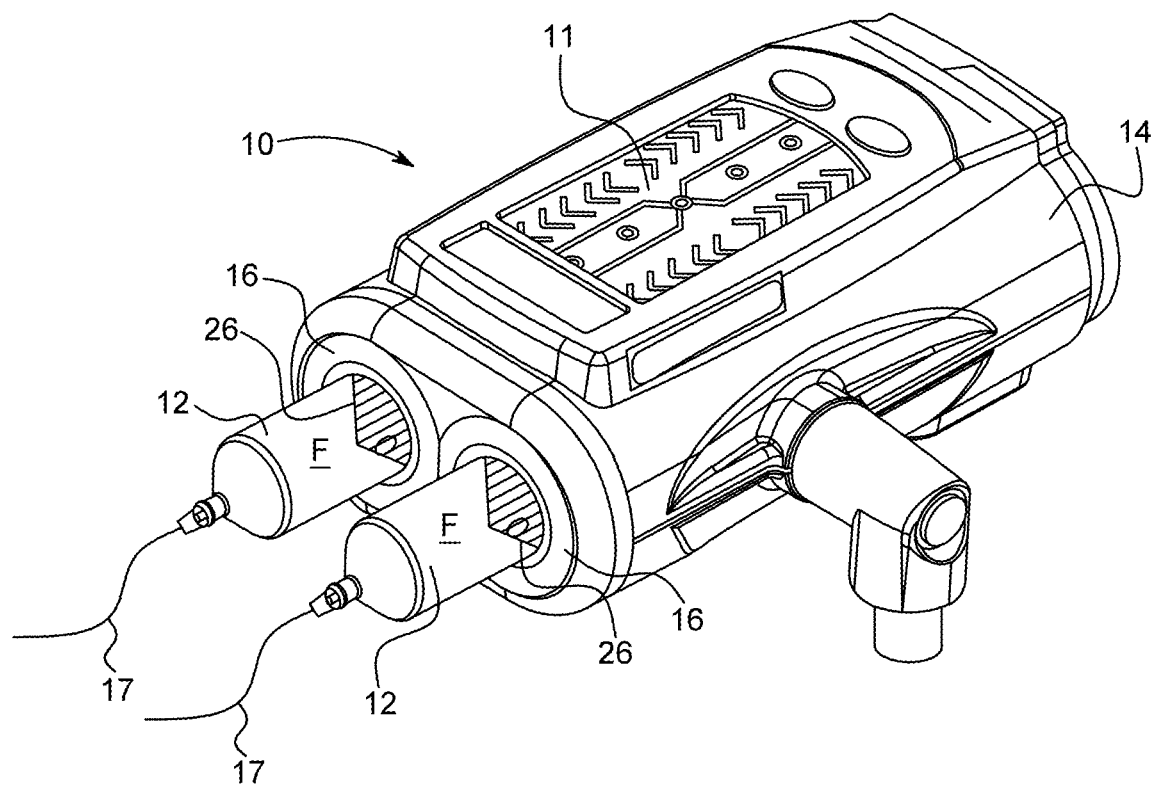
FIG. 1 is a top perspective view of a reader system including a fluid injector and at least one syringe according to an example of the present disclosure.

The illustrations generally show preferred and non-limiting examples of the systems and methods of the present disclosure. The following description is provided to enable those skilled in the art to make and use the described examples contemplated for carrying out the disclosure. While the description presents various examples of the devices, it should not be interpreted in any way as limiting the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

As used in the specification and the claims, the singular form of "a", "an", and "the" include plural referents unless the context clearly dictates otherwise.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The terms "first", "second", and the like are not intended to refer to any particular order or chronology, but instead refer to different conditions, properties, or elements.

All documents referred to herein are "incorporated by reference" in their entirety.

The term "at least" means "greater than or equal to." The term "not greater than" means "less than or equal to."

The term "includes" is synonymous with "comprises".

When used in relation to a syringe, the term "proximal" refers to a portion of a syringe nearest to an injector when a syringe is oriented for connecting to an injector. The term "distal" refers to a portion of a syringe farthest away from an injector when a syringe is oriented for connecting or is connected to an injector. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of a syringe extending between the proximal and distal ends.

It is to be understood, however, that the disclosure may assume alternative variations and step sequences, except where expressly specified to the contrary. It is also to be understood that the specific devices and processes illustrated in the attached drawings, and described in the following specification, are simply non-limiting examples of the disclosure. Hence, specific dimensions and other physical characteristics related to the examples (i.e., examples, variants, variations) disclosed herein are not to be considered as limiting.

Referring to the drawings in which like reference characters refer to like parts throughout the several views thereof, the present disclosure is generally directed to a syringe having an identification tag and an identification tag reader system for reading information stored in the identification tag.

Fluid Injector

With reference to FIG. 1, a fluid injector 10 (hereinafter referred to as "injector 10"), such as an automated or powered fluid injector, is adapted to interface with and actuate at least one syringe 12, each of which may be independently filled with a medical fluid F, such as contrast media, saline solution, or any desired medical fluid. The injector 10 may be used during a medical procedure to inject the medical fluid into the body of a patient by driving a plunger 26 of the at least one syringe 12 with at least one piston. The injector 10 may be a multi-syringe injector, wherein several syringes 12 may be oriented in a side-by-side or other arrangement and include plungers 26 separately actuated by respective pistons associated with the injector 10. In examples with two syringes arranged in a side-by-side relationship and filled with two different medical fluids, the injector 10 may deliver fluid from one or both of the syringes 12. The injector 10 has a control mechanism 11 configured for controlling operation of at least one operating parameter of the injector 10, such as the injection pressure and the volume of fluid delivered from at least one of the syringes 12.

The injector 10 has a housing 14 formed from a suitable structural material, such as plastic or metal, that encloses various components for delivering fluid from the syringes 12. The housing 14 may have various shapes and sizes depending on a desired application. For example, the injector 10 may be a free-standing structure configured to be placed on the floor with a stationary or movable platform. Alternatively, the injector 10 may be configured for placement on a suitable table or support frame. The injector 10 includes at least one syringe port 16 for connecting the at least one syringe 12 to respective piston elements. In some examples, the at least one syringe 12 includes at least one syringe retaining member for retaining the syringe 12 within the syringe port 16 of the injector 10. The at least one syringe retaining member operatively engages a locking mechanism provided on or in the syringe port 16 of the injector 10 to facilitate loading and/or removal of the syringe 12 to and from the injector 10, as described herein. The syringe retaining member and the locking mechanism together define a connection interface for connecting the syringe 12 to the injector 10.

At least one fluid path set 17 may be fluidly connected with the at least one syringe 12 for delivering medical fluid F from the at least one syringe 12 to a catheter, needle, or other fluid delivery device (not shown) inserted into a patient at a vascular access site. Fluid flow from the at least one syringe 12 may be regulated by a fluid control module (not shown). The fluid control module may operate various pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. One example of a suitable front-loading fluid injector 10 that may be modified for use with the above-described system including at least one syringe 12 and at least one syringe interface for self-oriented loading and releasable retaining of the at least one syringe 12 with the fluid injector 10 described herein with reference to FIG. 1 is disclosed in U.S. Pat. No. 5,383,858 to Reilly et al. and U.S. Pat. Nos. 9,173,995 and 9,199,033, each of which is incorporated herein by reference in their entirety. Another example of relevant multi-fluid delivery systems that may be modified for use with the present system is found U.S. Pat. No. 7,553,294 to Lazzaro et al.; U.S. Pat. No. 7,666,169 to Cowan et al.; International Patent Publication No. WO 2012/155035; and U.S. Pat. No. 9,474,857 to Riley et al.; the disclosures of which are incorporated herein by reference. Other examples may include new fluid injector systems designed to include various examples of the piston plunger interfaces described herein.

Syringe

Figure 2:
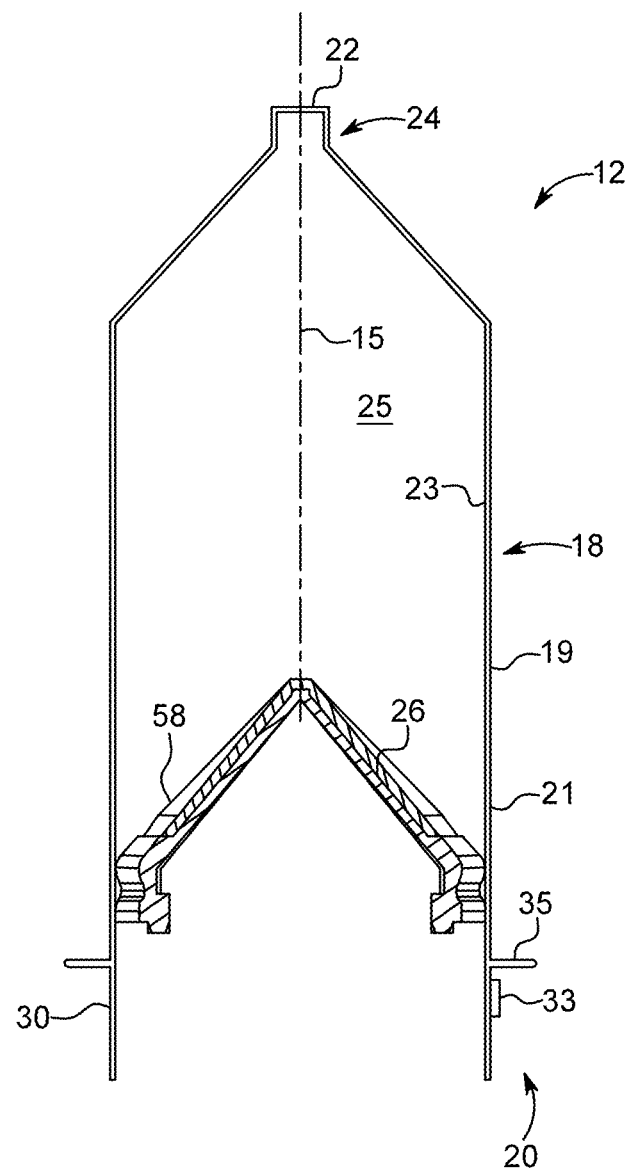
FIG. 2 is a side cross-sectional view of a syringe according to one example of the present disclosure.

Having described the general structure and function of the injector 10, the at least one syringe 12 will now be discussed in greater detail. With reference to FIG. 2, the syringe 12 generally has a cylindrical syringe barrel 18 formed from glass, metal, or a suitable medical-grade plastic. The barrel 18 has a proximal end 20 and a distal end 24, with a sidewall 19 extending therebetween along a syringe longitudinal axis 15 extending through a center of the barrel 18. The barrel 18 may be made from a transparent or translucent material. A nozzle 22 extends from the distal end 24 of the barrel 18. The barrel 18 has an outer surface 21 and an inner surface or wall 23 that defines an interior volume 25 for receiving the fluid therein. The proximal end 20 of the barrel 18 may be sealed with the plunger 26 that is slidable through the barrel 18. The plunger 26 may have a plunger cover 58 that forms a liquid-tight seal against the inner surface 23 of the sidewall 19 of the barrel 18 as the plunger 26 is advanced therethrough.

A drip flange 35 may extend radially outwardly from the outer surface 21 of the syringe barrel 18 relative to the longitudinal axis 15. The drip flange 35 may extend around at least a portion of the outer circumference of the barrel 18. The drip flange 35 may prevent fluid that drips from the nozzle 22 from entering the syringe port 16 on the injector 10. In this manner, the drip flange 35 helps reduce the amount of fluid that may enter the syringe port 16 and jam or otherwise interfere with the connection interface and/or the interior mechanics and electronics of the injector 10. In some examples, the drip flange 35 defines a stop surface that delimits the depth at which an insertion section 30 of the syringe 12 may be inserted into the syringe port 16 (shown in FIG. 1). The drip flange 35 may be formed integrally with the barrel 18 or it may be affixed or otherwise secured to the outer surface 21 of the barrel 18.

With continued reference to FIG. 2, the proximal end 20 of the syringe 12 is sized and adapted for being removably inserted in the syringe port 16 of the injector 10 (shown in FIG. 1). In some examples, the proximal end 20 of the syringe 12 defines the insertion section 30 that is removably insertable into the syringe port 16 of the injector 10 while the remaining portion of the syringe 12 remains outside of the syringe port 16.

Exemplary syringes suitable for use with the injector 10 depicted in FIG. 1 and which can be adapted for use with a fluid verification system are described in U.S. Pat. Nos. 9,173,995; 9,199,033; and 9,700,670, the disclosure of which is incorporated herein by reference in its entirety. Additional exemplary syringes are disclosed in, for example, U.S. Pat. No. 5,383,858 to Reilly et al., U.S. Pat. No. 6,322,535 to Hitchins et al., and U.S. Pat. No. 6,652,489 to Trocki et al., the disclosures of each of which is incorporated herein by reference in their entireties.

In certain examples, the proximal end 20 of the syringe 12 includes one or more syringe retaining members 33 adapted to form a locking engagement with a corresponding locking mechanism in the syringe port 16 of the injector 10 for releasably retaining the syringe 12 in the syringe port 16. Various retaining members 33 for releasably locking the syringe 12 with the injector 10 are described in, for example, U.S. Pat. Nos. 9,173,995; 9,199,033; and 9,700,670.

Identification Tag

Figure 3A:
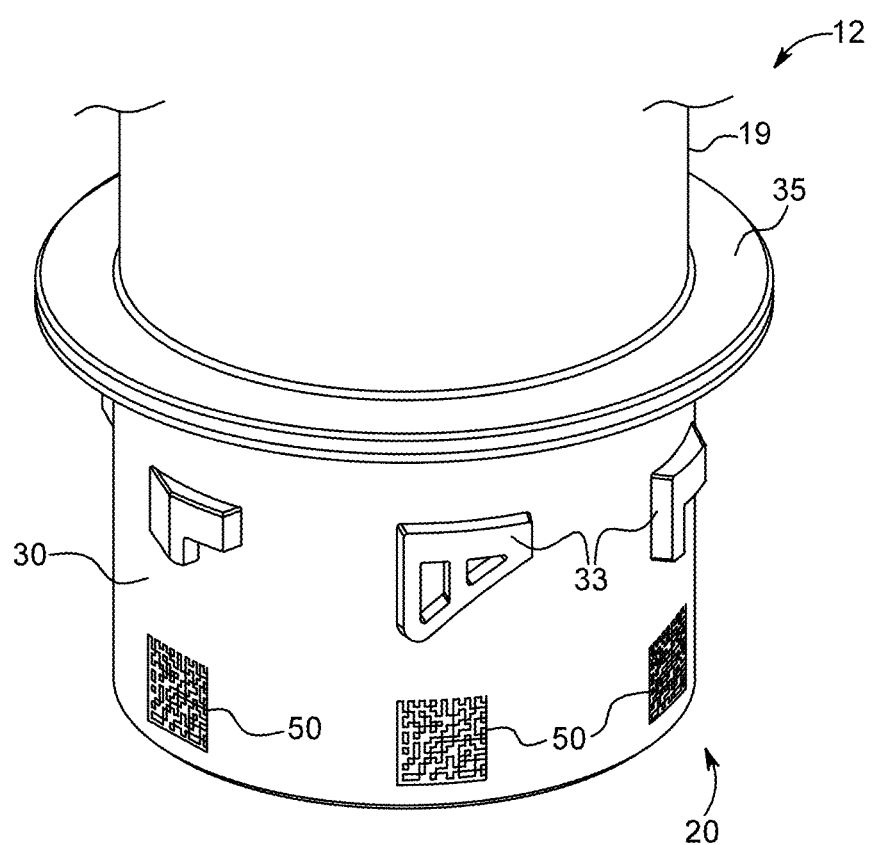
FIG. 3A is a perspective view of a proximal end of a syringe having an identification tag according to one example of the present disclosure.
Figure 3B:
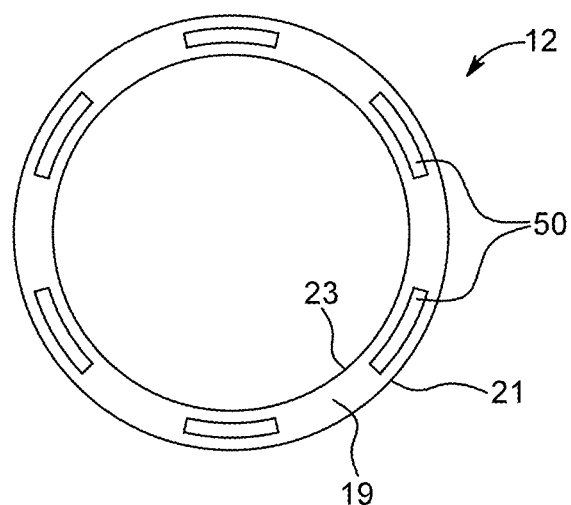
FIG. 3B is a detailed, top cross-sectional view of a proximal end of a syringe having an identification tag in accordance with another example of the present disclosure.
Figure 3C:
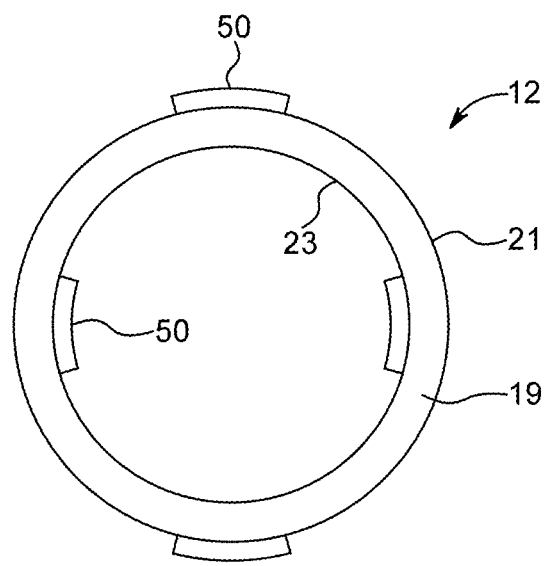
FIG. 3C is a detailed, top cross-sectional view of a proximal end of a syringe having an identification tag in accordance with another example of the present disclosure.

With reference to FIGS. 3A-3C, the syringe 12 has at least one identification tag 50 associated therewith. In specific embodiments, the syringe may have a plurality of identification tags 50, such as 2, 3, 4, 5, 6, 7, 8, 9, or 10 identification tags. In some examples, the at least one identification tag 50 may be positioned at the proximal end 20 of the syringe 12, such as on the insertion portion 30 proximal of the drip flange 35. In other examples, the at least one identification tag 50 may be positioned on any portion of the syringe barrel 18 between the proximal end 20 and the distal end 24. In some examples, the at least one identification tag 50 may be a 1-dimensional, 2-dimensional, or 3-dimensional barcode having information about at least one property of the syringe 12 and/or the fluid contained therein. In other embodiments, the at least one identification tag 50 may comprise a combination of 1-dimensional, 2-dimensional, and/or 3 dimensional barcodes. In certain embodiments, the at least one identification tag 50 may be a Q-R Code. In other examples, the at least one identification tag 50 may be indicia, such as words, marks, images, or other indicia having information about at least one property of the syringe 12 and/or the fluid contained therein.

While the at least one identification tag 50 is discussed herein as being associated with a syringe 12 in one preferred and non-limiting example, it should be noted that the use of the at least one identification tag 50 and a corresponding identification tag reader system is not limited to the syringe 12 and the fluid injector 10. For example, the at least one identification tag 50 may be provided on any transparent or translucent object. One of ordinary skill in the art would readily understand that the at least one identification tag 50 may be used with a variety of objects for storing information relating to at least one property of the object. For example, in certain embodiments, the at least one identification tag 50 may be on a transparent or translucent label adhered to at least a portion of the syringe 12.

With particular reference to FIG. 3A, the at least one identification tag 50 may be a plurality of identification tags 50 spaced apart from one another at equal or unequal angular intervals in a circumferential direction. For example, the syringe 12 may have six identification tags 50 spaced apart at equal angular intervals in a circumferential direction. In other examples, the at least one identification tag 50 may be a plurality of identification tags 50 spaced apart from one another at equal or unequal intervals in a circumferential and/or axial direction. Each of the plurality of identification tags 50 may be identical to one another (i.e., tags 50 may be encoded with identical information). Alternatively, the plurality of identification tags 50 may be different from one another (i.e., each tag 50 may be encoded with different information). Providing multiple identification tags 50 in a circumferential direction of the syringe 12 assures that at least a portion of at least one of the at least one identification tags 50 can be read by a detector of the reader system of the fluid injector 10, as described herein.

With continued reference to FIG. 3A, according to certain embodiments each syringe 12 may have a unique set of identification tags 50 that contain identifying information about at least one property of the syringe 12 and/or the fluid contained therein. In some examples, the at least one identification tag 50 may be approximately 0.312×0.312 inches, although other sized identification tags are contemplated, for example depending on the available surface area on the transparent surface, the amount of information encoded into the identification tag 50, and/or the field of view of the detector. The at least one identification tag 50 may have an array of symbols, for example in a 36×36 data matrix format such that the at least one identification tag 50 is capable of storing 128 bytes (1,024 bits) of data. Other symbol arrays are contemplated dependent on the amount of information encoded into the identification tag 50. In some examples, information that can be stored in the at least one identification tag 50 includes, without limitation, information regarding the syringe type, such as size, pressure rating, multi—or single-patient use, and/or use with a particular injector platform. In other examples, information that can be stored in the at least one identification tag 50 includes, without limitation, information regarding production data of the syringe, such as the date and time of manufacture, lot number, production line, plant code, and/or shelf life. In other examples, information that can be stored in the at least one identification tag 50 includes, without limitation, information regarding the type of fluid stored in the syringe, volume of fluid, and/or shelf life. In other examples, information that can be stored in the at least one identification tag 50 includes, without limitation, information regarding a unique digital signature that can be verified by the fluid injector 10 to confirm that an authentic syringe 12 is used with the fluid injector 10 or that the syringe that has been approved for use with the injector system by the manufacturer of the injector. Any and all of this information may be stored in each of the at least one identification tag 50 or a combination of 2 or more of the at least one identification tags.

In some examples, the at least one identification tag 50 may be engraved or etched within the sidewall 19 of the syringe 12 such that the at least one identification tag 50 is positioned between the inner sidewall 23 and the outer sidewall 21 as illustrated in FIG. 3B. For example, the at least one identification tag 50 may be laser-etched within the thickness of the sidewall 19 of the syringe 12, such that the at least one identification tag 50 is positioned between the surfaces of the outer sidewall 21 and the inner sidewall 23. In this manner, any particulate matter from the syringe sidewall 19 generated during laser etching or manufacture of the at least one identification tag 50 can be contained within the sidewall 19 and prevented from contaminating the inner sidewall 23 and/or outer sidewall 21 of the syringe 12. Further, etching the identification tag 50 within the thickness of the side wall 19 may prevent tampering with or altering the information contained in the identification tag 50.

In other examples, the at least one identification tag 50 may be positioned on the surface of the inner sidewall 23 and/or the outer sidewall 21 of the syringe 12 (FIG. 3C). For example, the at least one identification tag 50 may be etched, engraved, or machined on the surface of the inner sidewall 23 and/or the outer sidewall 21 of the syringe 12. In other examples, the at least one identification tag 50 may be printed directly on the syringe 12, or it may be printed on a carrier which is adhesively or otherwise affixed to the inner sidewall 23 and/or the outer sidewall 21 of the syringe 12. In some examples, the at least one identification tag 50 may be formed on the inner sidewall 23 or the outer sidewall 21 of the syringe 12 using a thermal transfer printing technique. In other embodiments, the at least one identification tag 50 may be printed on a label that may then be affixed, such as adhesively or shrink-wrapped, to or around the outer sidewall 21 or the inner sidewall 23.

Identification Tag Reader System

Figure 4A:
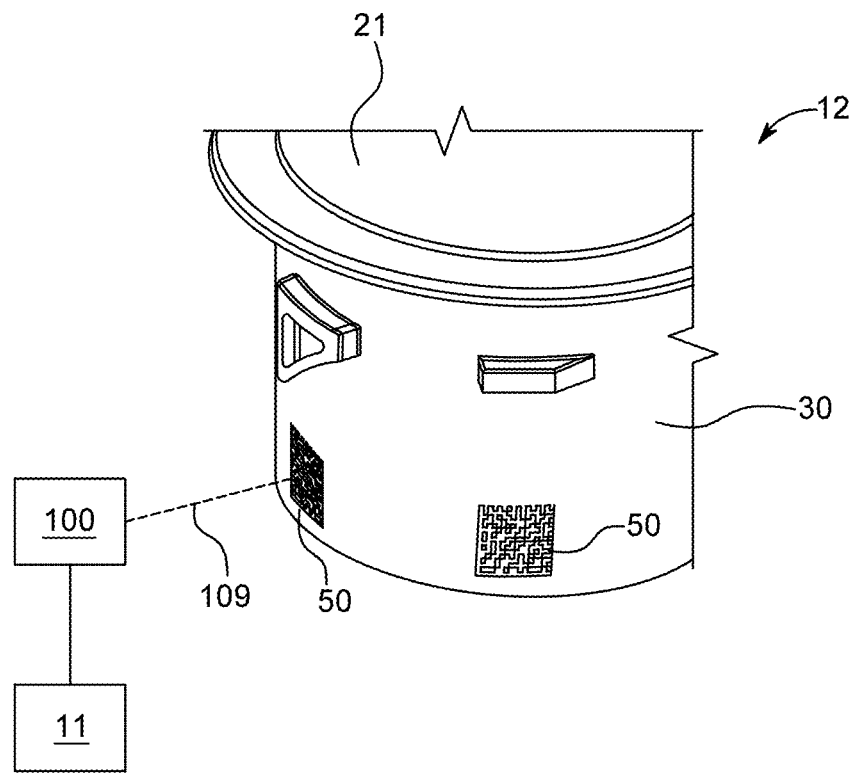
FIG. 4A is a perspective view of the syringe shown in FIG. 3A along with a reader system for reading the identification tag in accordance with one example of the present disclosure.

With reference to FIG. 4A, the injector 10 (shown in FIG. 1) has at least one identification tag reader system 100 (hereinafter referred to as "reader system 100") configured for reading information from the at least one identification tag 50 on the syringe 12. According to certain embodiments, at least one reader system 100 may be associated with each syringe port of an injector. In various examples, the reader system 100 may be an optical system, such as a video- or a still-image system. In other examples, the reader system 100 may be a laser-based system. In each example, the reader system 100 is configured to detect at least one of the at least one identification tags 50 on the syringe 12, and read/decode information contained within the at least one identification tag 50, for example by a control mechanism 11. The read/decoded information can be used by the injector 10 for controlling at least one operating parameter of the injector 10.

While the reader system 100 is discussed herein as being associated with the injector 10 in one preferred and non-limiting example, it should be noted that the use of the reader system 100 is not limited to the injector 10. For example, the reader system 100 may be a standalone system configured for reading at least one identification tag 50 provided on any transparent or translucent object. Alternatively, the reader system 100 may be associated with any other system wherein the reader system 100 provides an additional functionality to the system by enabling reading of information stored in the at least one identification tag 50.

The reader system 100 may be provided inside the housing 14 of the injector 10 and is operatively connected to the control mechanism 11 of the injector 10 such that the reader system 100 can receive instructions from the control mechanism 11 and send information to the control mechanism 11. For example, the control mechanism 11 may be configured to control the operation of the reader system 100. In some examples, the reader system 100 may be controlled independently of the control mechanism 11 of the injector 10. In such examples, the reader system 100 may be configured to communicate with the control mechanism 11 and send information from the at least one identification tag 50 to the control mechanism 11 for controlling operation of at least one parameter of the injector 10.

With continued reference to FIG. 4A, at least a portion of the reader system 100 may be positioned radially offset relative to the outer surface 21 of the syringe 12 such that the reader system 100 is positioned opposite at least one identification tag 50. In such examples, the reader system 100 is positioned such that at least one of the at least one identification tags 50 is in a direct optical path 109 of the reader system 100. In various embodiments, one or more lenses (not shown) and/or mirrors may be used in an optical path 109 between the reader system 100 and the at least one identification tag 50 to enlarge or reduce the size of the at least one identification tag 50.

Figure 4B:
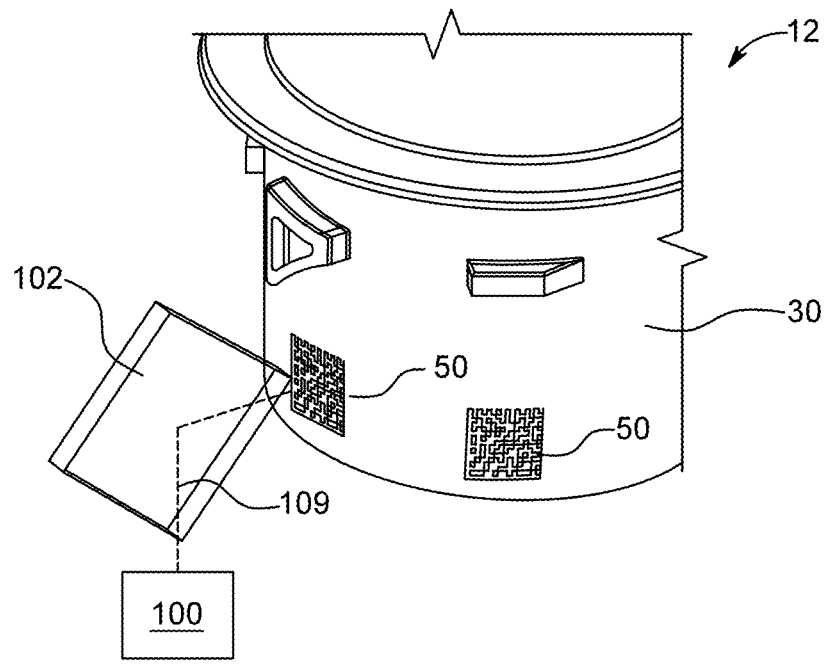
FIG. 4B is a perspective view of the syringe shown in FIG. 3A along with a reader system for reading the identification tag in accordance with another example of the present disclosure.

In other examples, such as shown in FIG. 4B, the reader system 100 may be offset axially and radially relative to the outer surface 21 of the syringe 12. In such examples, the reader system is positioned such that the at least one identification tag 50 is outside a field of view of the reader system 100. One or more reflective elements 102, such as mirrors, may be provided to fold or direct the optical path 109 between the reader system 100 and at least one of the at least one identification tag 50. In some examples, the one or more reflective elements 102 may be a front surface mirror (with the silvering applied to the exposed front surface of the glass), or a rear surface mirror. The use of a front surface mirror may be used in certain embodiments because undesirable secondary or "ghost" reflections that may occur with rear surface mirrors can be eliminated. The one or more reflective elements 102 may be flat, convex, or concave or a combination of any of these geometries, for example with more than one reflective element 102 is used. In this manner, the size of the at least one identification tag 50 that is perceived by the reader system 100 may be enlarged or reduced as required to fit within the detection area of the reader. In addition, one or more lenses (not shown) may be used in optical path 109 between the reader system 100 and the at least one identification tag 50 to further enlarge or reduce the size of the at least one identification tag 50.

The one or more reflective element 102 may be placed in an optical path 109 so that the optical path 109 clearly exposes at least one of the at least one identification tags 50 to the reader system 100. For example, in certain embodiments where the at least one identification tag 50 and the reader system are orthogonal, for example to allow all of the components of the reader system 100 to fit within a confined space within the injector housing 14, the system may utilize a reflective element at about a 45° angle to direct the optical path from the reader system 100 to the at least one identification tag 50. By bending the optical path 109, for example through a 90° angle, the orientation of the reader system 100 may be effectively rotated to face toward the distal end 24 of the syringe 12 (shown in FIG. 4B). In some examples, it may be desirable to position the reflective element 102 at about an angle of 45° to create a 90° bend in the optical path 109. The optical path 109 may be as close to perpendicular relative to the at least one identification tag 50. Such positioning of the reflective element 102 may eliminate any blurring of the at least one identification tag 50 due to an optical path 109 that is not perpendicular. An off-axis alignment of the optical path 109 may cause a top portion of the at least one identification tag 50 to appear either wider or more narrow than a bottom portion, making it more difficult to detect and decode the identification tag 50, although this may be corrected for in the reader system software if necessary.

Figure 14A:
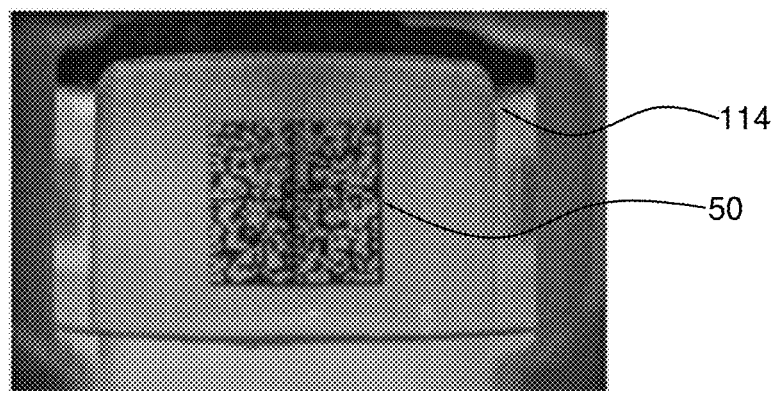
FIGS. 14A-14C show an identification tag read by a syringe identification module with various levels or types of illumination.
Figure 14B:
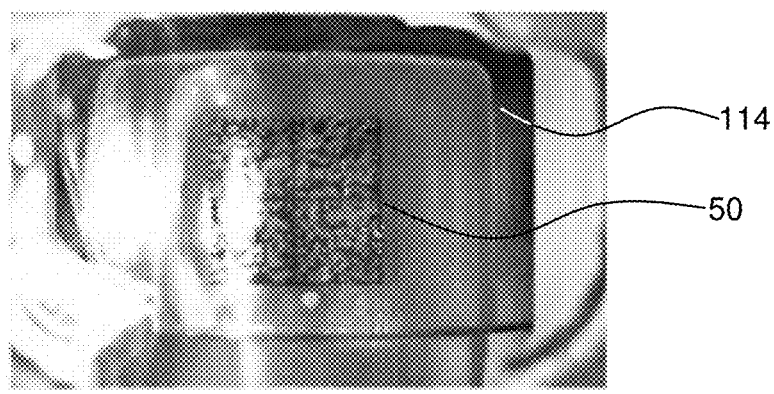
Figure 14C:
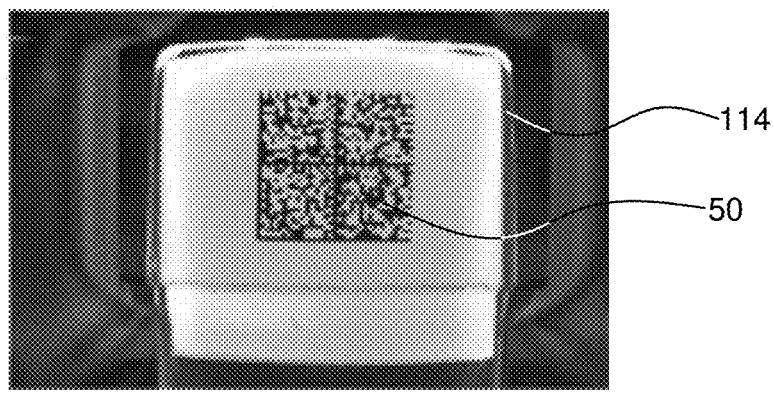

Due to positioning of the at least one identification tag 50 on the insertion portion 30 of the syringe 12, the at least one identification tag 50 is positioned within the syringe port 16 when the syringe 12 is connected to the injector 10. Due to the enclosed configuration of the syringe port 16, the insertion portion 30 of the syringe 12 is in a dark environment with little to no ambient light. As such, the at least one identification tag 50 is also in the dark environment. Imaging of the at least one identification tag 50 in a dark environment makes it difficult or impossible to capture sufficient detail from the at least one identification tag 50 in order to extract the necessary information therefrom (see FIG. 14A). Lighting of at least a portion of at least the at least one identification tag 50 within the optical path to increase the contrast of the at least one identification tag 50 against the surrounding background is important in various embodiments for successful and reliable reading of information stored in the at least one identification tag 50, particularly within a dark environment such as the interior of the injector 10. The dark environment within the syringe port 16 poses several challenges for reading the at least one identification tag 50 using the reader system 100. According to various embodiments, the at least one identification tag 50 must be illuminated, or otherwise visually enhanced, before it can be detected or effectively read by the reader system 100. Directly illuminating the identification tag 50 may result in glare from the smooth and reflective surface of the syringe 12 (see FIG. 14B). Furthermore, focusing on the at least one identification tag 50 can be difficult due to the curved shape of the syringe barrel 18. In addition, the transparent syringe barrel material may appear to be dark with some illumination strategies, thereby providing little contrast with the dark identification tag 50. It has been found through experimentation that illuminating a background behind the at least one identification tag 50 provides an optimum amount of contrast between the at least one identification tag 50 and the background environment to enable efficient and reliable reading of information embedded in the at least one identification tag 50 (see FIG. 14C).

Figure 5:
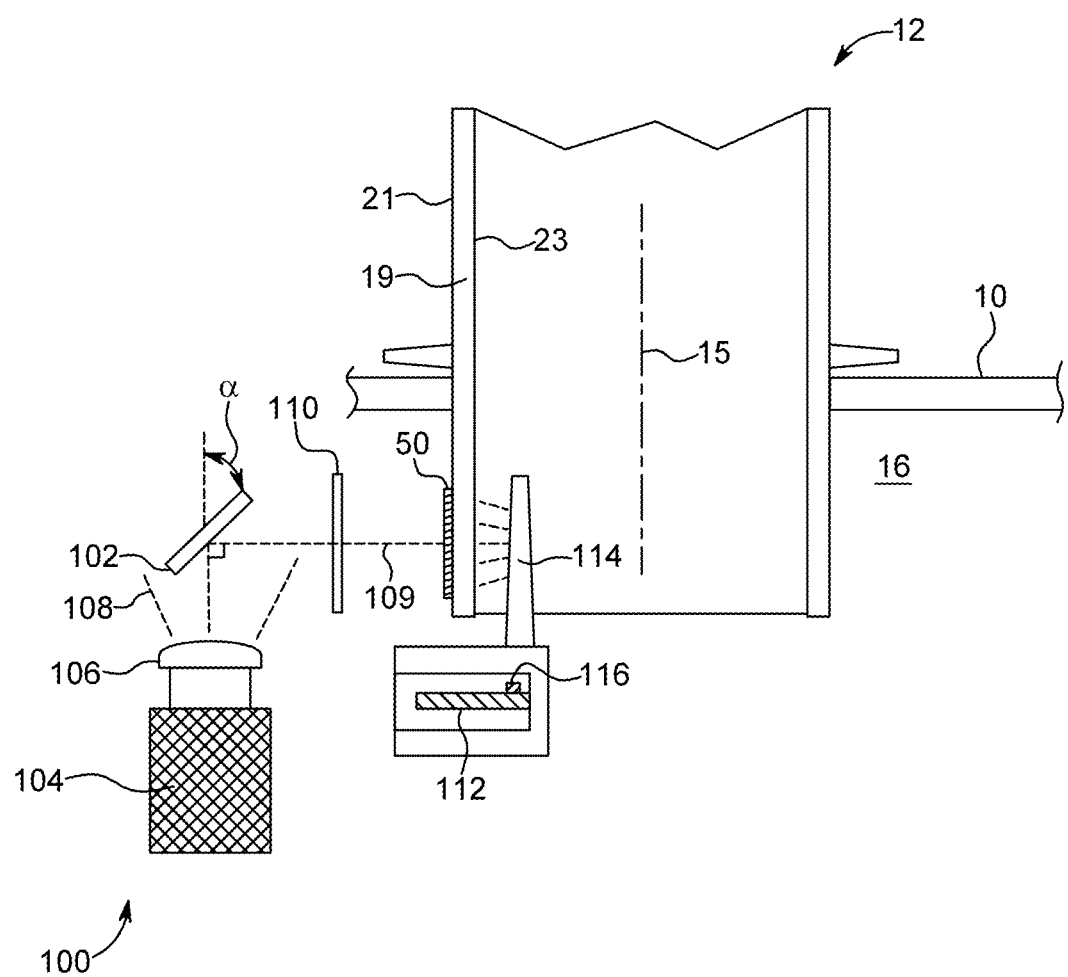
FIG. 5 is a schematic illustration of a syringe having an identification tag and an identification tag reader system in accordance with one example of the present disclosure.

With reference to FIG. 5, according to certain embodiments the reader system 100 may have a detector 104, such as an optical scan engine or camera, having a lens 106. The detector 104 may be arranged such that its field of view 108 is in a direction substantially parallel with the longitudinal axis 15 of the syringe 12. The reader system 100 may further have at least one reflective element 102 to "fold" or direct the optical path 109 between the detector 104 and at least one of the at least one identification tag 50 on the syringe 12. The at least one reflective element 102 may be positioned at an angle α relative to the longitudinal axis 15 of the syringe 12. According to certain embodiments, the angle α may be from about 44° to about 46°. The at least one reflective element 102 is desirably positioned at an angle of about 45° to create a 90° bend in the optical path 109 to eliminate blurring of the at least one identification tag 50. While the identification tag 50 is illustrated as being on the outer surface 21 of the syringe 12, in other embodiments the identification tag 50 may be disposed between the outer surface 21 and the inner surface 23 of the syringe 12 or one the inner surface 23 of the syringe 12, such as shown in FIGS. 3B and 3C. In certain embodiments, a protective window 110 may be disposed between the reflective element 102 and the outer surface 21 of the syringe 12, for example to protect the optical components of the system from fouling from medical fluids, such as contrast, which may impair the ability of the system to effectively read the at least one identification code 50. The reader system 100 may further have an illumination system 112 for illuminating at least a portion of the at least one identification tag 50. In some examples, the illumination system 112 may be configured to illuminate at least a portion of a background screen 114 situated behind the at least one identification tag 50 such that the at least one identification tag 50 is disposed between the illuminated background screen 114 and the optical path 109 of the detector 104. The illumination system 112 may have one or more light modules 116, such as light emitting diodes (LEDs), laser, or other light source, which illuminate at least a portion of the background screen 114. In some examples, the background screen 114 may be a "light pipe" positioned within an interior of syringe 12 behind the at least one identification tag 50 and directing light from the one or more light modules 116 up through the background screen 114.

Figure 6:
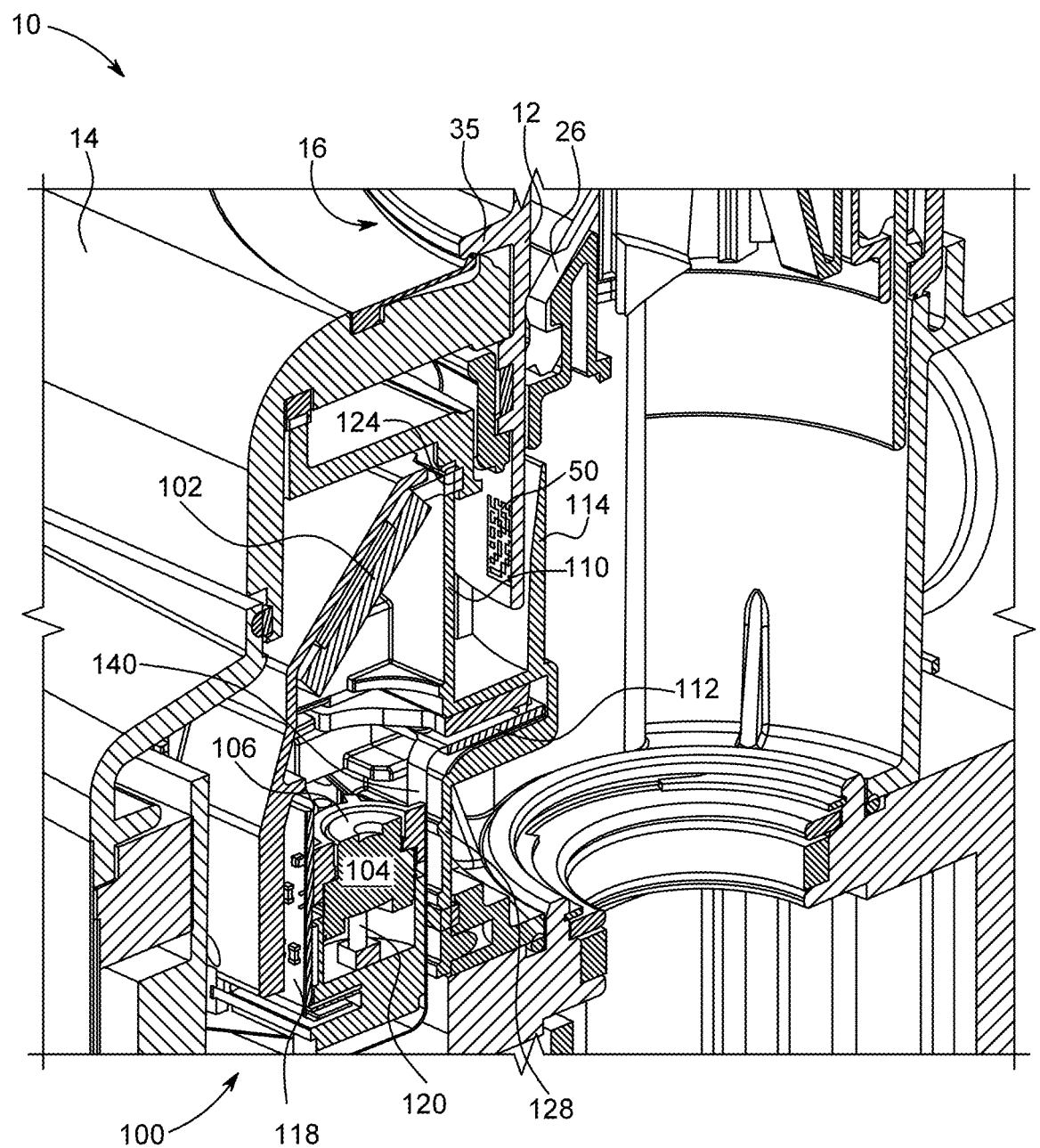
FIG. 6 is a perspective cross-sectional view of a syringe having an identification tag connected to a fluid injector having an identification tag reader system in accordance with one example of the present disclosure.

With reference to FIG. 6, the reader system 100 according to an embodiment is shown as it is positioned within the injector housing 14 with syringe 12 inserted into the syringe port 16. The reader system 100 may have an interface board 118 for controlling operation of the reader system 100. For example, the interface board 118 may be connected to the detector 104 and/or the illumination system 112 by one or more cables 120 and 140. The detector 104 and/or the illumination system 112 may be contained within a housing 122 and/or a frame 128 that is received within a cavity within the injector housing 14 adjacent syringe port 16. The housing 122 may have at least one sealing element 124, such as an O-ring, for sealing the interior of the housing 122 from intrusion and fouling by dust particles and/or fluid.

Reader Module

Figure 7A:
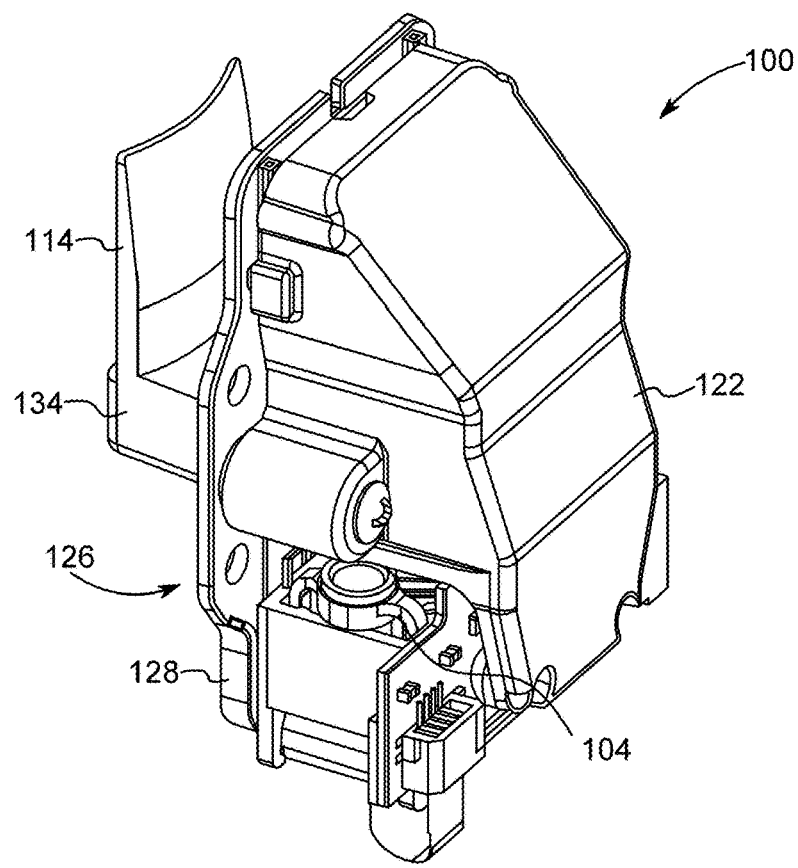
FIG. 7A is a perspective view of a syringe identification module in accordance with one example of the present disclosure.
Figure 7B:
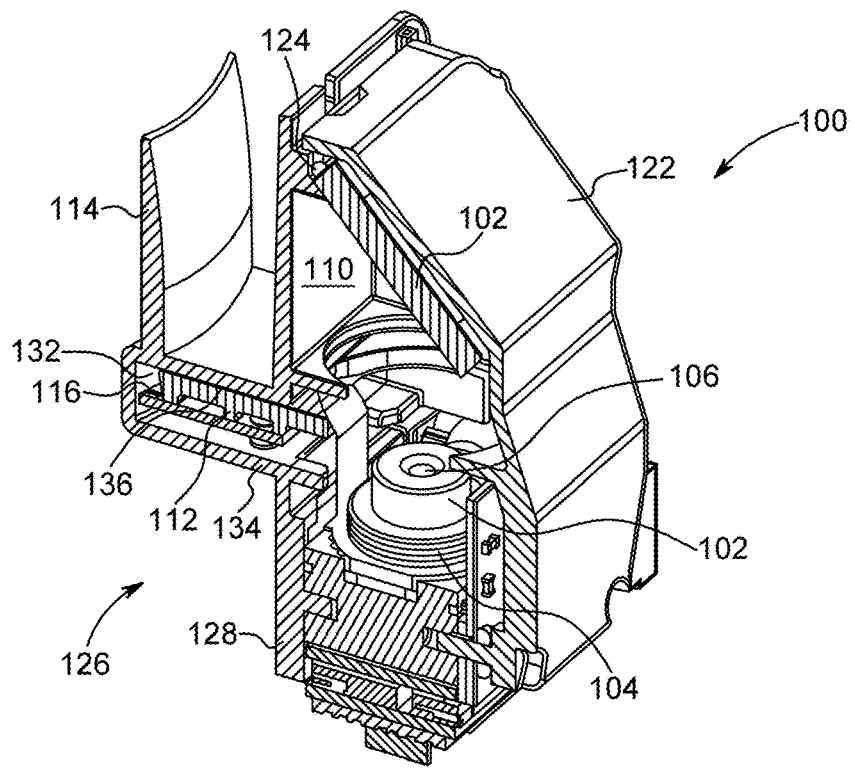
FIG. 7B is a cross-sectional view of the syringe identification module shown in FIG. 7A.

With reference to FIGS. 7A-7B, the reader system 100 may be configured as a reader module 126 having the housing 122 that receives the components of the reader system 100. In some examples, the reader module 126 may have a housing 122 that encloses and protects the detector 104 and the illumination system 112. The reader module 126 may further have the frame 128 for mounting at least one of the detector 104 and the illumination system 112. In certain embodiments, the background screen 114 may be integral with at least one of the housing 122 and the frame 128. Together, the housing 122 and the frame 128 align the components of the reader system 100 relative to the at least one identification tag 50 on the syringe 12 that appears within the field of view when the syringe 12 is inserted into the syringe port 16. The housing 122 and the frame 128 desirably enclose the components of the reader system 100 to prevent dust and contaminants from settling on and/or fouling the reflective element 102, the lens 106, or the inside surface of the protective window 110. The housing 122 and/or the frame 128 may be configured to position the reflective element 102 as closely to the detector 104 and the lens 106 as possible to prevent dust on the reflective element 102 from appearing as sharply focused spots. In certain embodiments, the injector 10 may have a plurality of reader modules 126 in each syringe port 16 to facilitate reading of the at least one identification tag 50 regardless of the rotational orientation of the syringe 12 about its longitudinal axis 15 relative to a longitudinal axis of the syringe port 16. For example, at least two reader modules 126 may be provided for each syringe port 16. In other embodiments, the injector 10 may include one reader module 126 within each syringe port 16 and the injector 10 may be configured to rotate or align the syringe upon insertion to place at least one of the at least one identification tags 50 within the field of view of the reader module 126.

With particular reference to FIG. 7B, the protective window 110 may be formed directly on one of the housing 122 and the frame 128. The protective window 110 is desirably transparent to allow an unobstructed optical path 109 (shown in FIG. 5) from the detector 104 to the at least one identification tag 50. The protective window 110 also protects the components of the reader system 100 from spilled contrast and other fluids or dust. The protective window 110 may be sealed to sealing element 124. Desirably, the protective window 110 is positioned as far from the at least one identification tag 50 as possible to prevent dirt and contamination on the protective window 110 from being in sharp focus.

Interface Board

With reference to FIG. 6, the interface board 118 may be in electronic communication with the control mechanism 11 of the injector 10. The interface board 118 communicates with the control mechanism 11 and may send and receive instructions thereto or control the operation thereof. The interface board 118 may have a microprocessor and associated software configured to convert the information from the at least one identification tag 50 into individual parameters. In some examples, the interface board 118 may have memory to store the unique identifying information of all recently used syringes 12. In this manner, the fluid injector 10 can be configured to prevent or provide a warning against reuse of a syringe 12 that has been used once or for a predetermined number of times. In other examples, the interface board 118 may have a decryption code to decrypt the unique identifying information associated with the at least one identification tag 50, for example to decode identifying information, as described herein, about the syringe, enable operation of the fluid injector 10 when a syringe 12 having the correct digital signature is connected and/or disable or provide a warning to the user when the syringe 12 does not have a correct digital signature. In addition, the interface board 118 may control the operation of the detector 104 and/or the illumination system 112 by way of one or more electronic connection cable 140. For example, the interface board 118 may control the timing and/or intensity of the LEDs, the aperture of the lens 106 and exposure time of the detector 104, or any other function associated with the detector 104 and/or illumination system 112 necessary for accurate reading of the at least one identification tag 50. In certain embodiments, the interface board 118 may be incorporated into the electronics of the fluid injector 10 and the reader system 100 may be connected to the fluid injector electronics by one or more electrical cables (not shown).

Detector

In some examples, the detector 104 may be a digital camera configured to capture an image of at least one identification tag 50, identify and extract information defining the at least one identification tag 50, and convert the identification tag 50 into usable data to be transmitted to the fluid injector 10, for example via the interface board 118 and/or the control mechanism 11. In specific embodiments, the detector 104 may have a color or black-and-white image sensor having a pixel resolution sufficient to detect and decode the at least one identification tag 50, for example a resolution of 752×480 pixels or more. In other embodiments, for example with larger or less complex identification tags 50, the resolution of the detector 104 may be less. The detector 104 may have a fixed or adjustable lens 106 suitable for focusing on the identification tag 50 within the field of view. In some examples, the lens may be a 6.20 mm f/2.8 lens or one with greater or lesser focus power. The detector 104 is operatively connected to the interface board 118. In this manner, information detected by the detector 104 may be communicated to the interface board 118 and to the fluid injector 10 including the fluid injector controller.

In some examples, the detector 104 may have a decoder with a microprocessor running firmware that is configured to decode the captured image of the identification tag 50 into numerical, alpha-numerical, or binary data. In some examples, the detector 104 may have one or more lighting elements (not shown), such as one or more light LEDs configured to illuminate the identification tag 50 during the scanning process. In some examples, the one or more lighting elements may be used to define an aiming pattern or dot on the identification tag 50.

Due to space constraints, in certain embodiments the detector 104 may have a short focal length that allows the detector 104 to be placed close to the syringe barrel 18. The detector 104 may also have a shallow depth of field such that the at least one identification tag 50 is in focus, while the remaining objects in the optical path 109, such as any dirt on the surface of the lens 106 or dirt on the outer surface 21 or the inner surface 23 of the syringe barrel 18, is out of focus. In some examples, the lens 106 of the detector 104 may be a magnifying lens that enlarges the size of the at least one identification tag 50 as seen by the detector 104. In other examples, the reader system 100 may have one or more magnifying lenses (not shown) external to the detector 104 to enlarge the size of the at least one identification tag 50 as seen by the detector 104. Maximizing the apparent size of the at least one identification tag 50 allows the available resolution of the detector 104 to be used most efficiently. In some examples, the detector 104 has a large aperture lens (e.g., f/2.0 or greater) to provide a shallow depth of field with increased light sensitivity.

Background Screen

Figure 8:
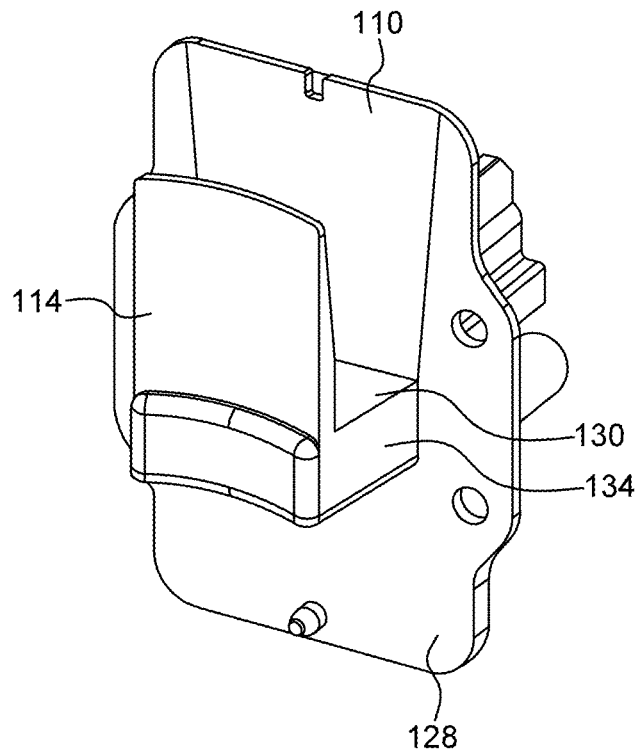
FIG. 8 is a perspective view of a frame and a light pipe of the syringe identification module shown in FIG. 7A.

With reference to FIG. 8, in certain embodiments the background screen 114 may be directly connected to the frame 128, such as by way of the spacer 134. In some examples, the background screen 114 and the spacer 134 are monolithically formed with the frame 128. In other examples, the background screen 114 and/or the spacer 134 are removably or non-removably connected to the frame 128. The background screen 114 is separated from the protective screen 110 by a space 130. When connected to the injector 10, at least a portion of the circumferential sidewall 19 of the insertion portion 30 of the syringe 12 is positioned in the space 130 between the protective screen 110 and the background screen 114 (see, e.g., FIG. 6). Additionally, the background screen 114 extends into the interior of the syringe barrel 18 such that it is positioned proximally of the plunger 26 when the plunger 26 is at its most proximal position. Further, the background screen 114 is positioned so that it does not interfere with the travel path of the injector piston (not shown). In this manner, the background screen 114 can be positioned behind at least one of the at least one identification tags 50 of the syringe 12 to provide an illuminated backdrop against which the identification tag 50 can be read by the reader module 126.

Figure 11:
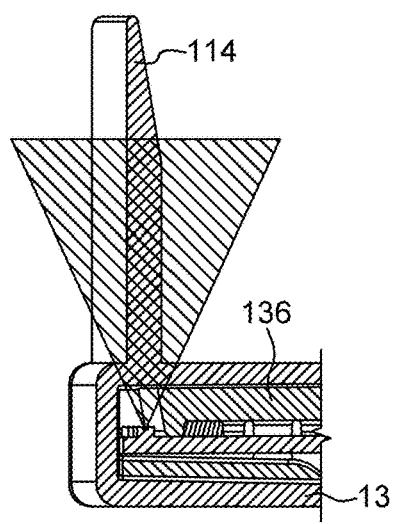
FIG. 11 is a side cross-sectional view of a lighting pattern projected on a light pipe by a lighting module of a syringe identification module.

The background screen 114 defines a surface behind the at least one identification tag 50 that can be illuminated with the illumination system 112 (shown in FIG. 9) to provide a contrasting background to the identification tag 50. In some examples, the background screen 114 is configured as a light pipe wherein light from the illumination system 112 is directed through the body of the background screen 114 in a proximal-to-distal direction (FIG. 11). The background screen 114 may be positioned directly above the illumination system 112 and may extend at an angle that is substantially parallel to a direction of illumination from the illumination system 112. In this manner, light from the illumination system 112 illuminates a bottom surface of the background screen 114 and is transmitted through the body of the background scree 114, thereby lighting at least a portion of the background screen 114. The at least one identification tag 50 can be read against a contrasting backdrop without directly illuminating the at least one identification tag 50 thereby reducing glare of the sidewall surface of the syringe 12. The background screen 114 may have at least one of an at least partially textured surface, an at least partially painted or coated surface, or a combination thereof. In some examples, the background screen 114 may be white in color to provide a high contrast background against which the identification tag 50 may be read. In other embodiments, the background screen 114 may be of a transparent or translucent material. In other embodiments, the background screen may have particulate material embedded within the screen material which may act to scatter at least a portion of the light as it passes through the body of the background screen 114. In certain embodiments, the background screen 114 is painted or coated with a material that is resistant to damage from exposure to contrast. In some examples, the background screen 114 may be curved to substantially correspond to a lateral curvature of the syringe barrel 18. On certain embodiments, the background screen 114 may be made from a transparent plastic with an opaque pigment added (such as white titanium dioxide powder, for example approximately 0.5% to 2%) or a fluorescent material added that fluoresces when exposed to light of a specific wavelength transmitted by the illumination system 112. When the pigment is illuminated by light from the illumination system 112, the background screen 114 will appear to glow internally. Furthermore in certain embodiments, the background screen 114 may narrow in a direction from a proximal end toward a distal end. In other embodiments, the background screen 114 may be made from a transparent plastic with a substantially transparent material added thereto which scatters at least a portion of the light when illuminated.

Figure 13:
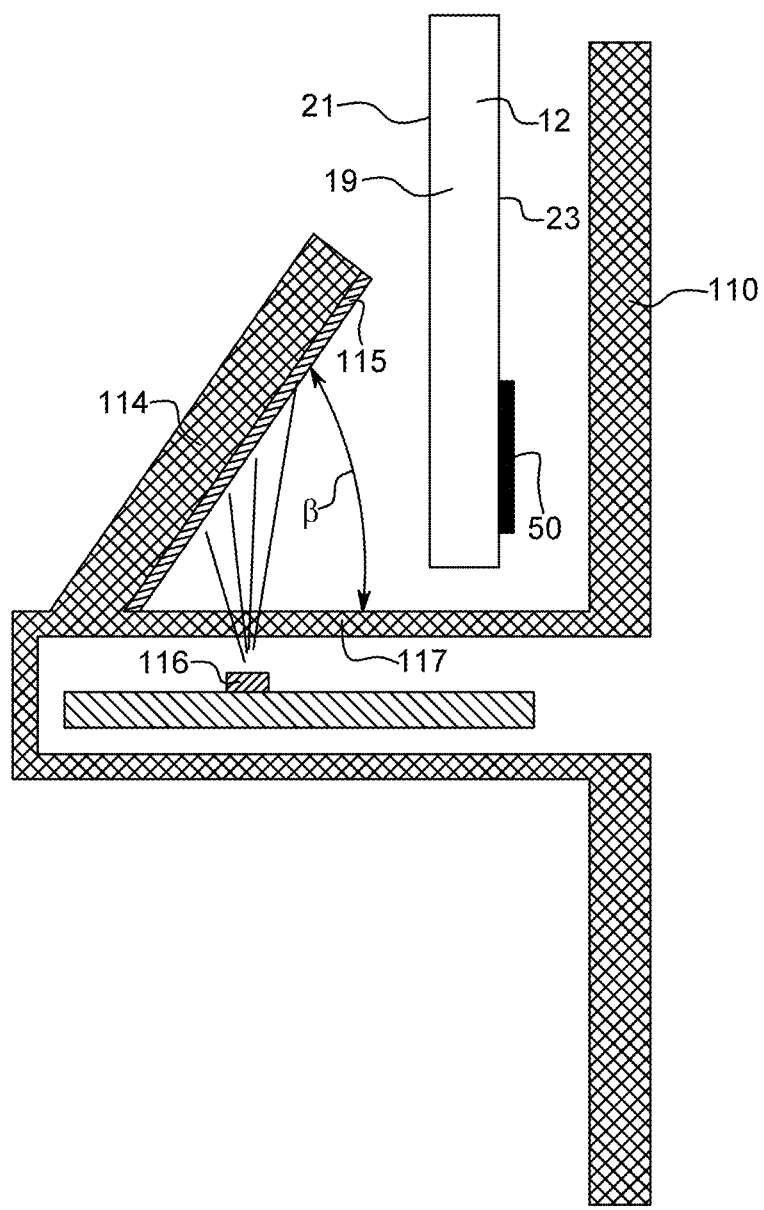
FIG. 13 is a side cross-sectional view of a background screen and illumination system in accordance with another example.

With reference to FIG. 13, the background screen 114 is shown in accordance with another example. The background screen 114 is angled relative to a direction of illumination from the one or more light modules 116 at an angle β. In some examples, the angle β may be 30° to 45° from the direction of illumination from the one or more light modules 116, which may be parallel with a lateral axis. The background screen 114 may have at least one painted surface 115 on a side closest to the at least one identification tag 50 to provide a high contrast background against which the identification tag 50 may be read. In some examples, the painted surface 115 may be white in color. The background screen 114 may be made from a transparent, translucent, or opaque material. Light from the one or more light modules 116 passes through a transparent cover 117 that supports the background screen 114 and is absorbed/reflected from the angled painted surface 115 of the background screen 114 to illuminate a background behind the at least one identification tag 50. While the at least one identification tag 50 is illustrated in FIG. 13 as being positioned on an inner surface 23 of the syringe 12, it should be noted that the at least one identification tag 50 may also be positioned on an outer surface 21 of the syringe 12, such as shown in FIG. 3C, or within the sidewall 19 of the syringe 12 between the outer surface 21 and the inner surface 23, such as shown in FIG. 3B.

Illumination System

Figure 9:
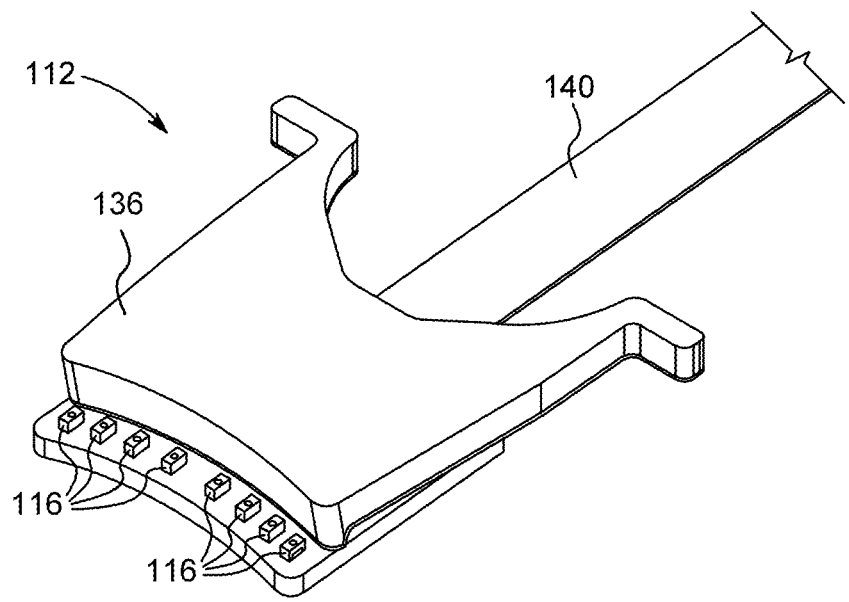
FIG. 9 is a perspective view of a lighting module of the syringe identification module shown in FIG. 7A.
Figure 10:
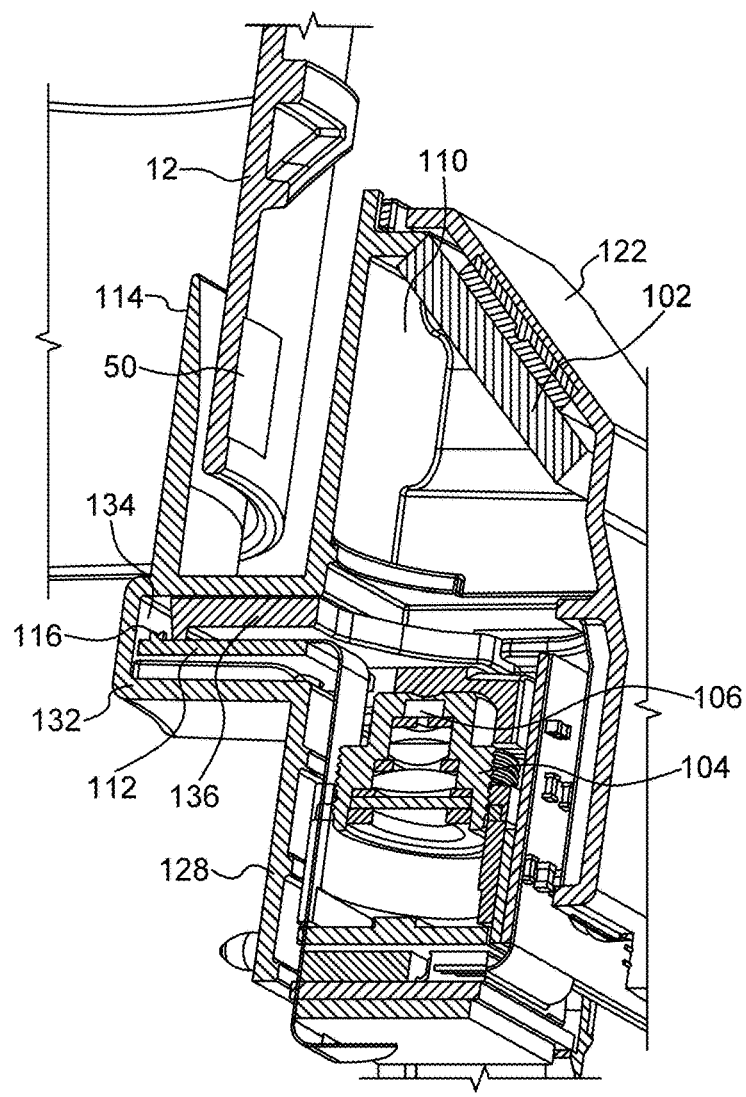
FIG. 10 is a perspective cross-sectional view of syringe identification module and a syringe having an identification tag.

With reference to FIG. 9, according to various aspects, the illumination system 112 may have a plurality of light modules 116, such as LEDs, lasers, or other light source. As shown in FIG. 7B, the illumination system 112 may be positioned within a cavity 132 of the spacer 134 between the frame 128 and the background screen 114. In some examples, the plurality of light modules 116 may be positioned directly under a proximal end of the background screen 114 such that light from each of the plurality of light modules 116 is directed toward the background screen 114. The position of the plurality of light modules 116 is selected to maximize the amount of light illuminating the proximal end of the background screen 114, and therefore travelling up through the interior portion of the background screen 114 creating a light pipe effect. In some examples, such as shown in FIGS. 10-11, a shield 136 may be provided to block at least a portion of the light emitted by the plurality of light modules 116 that does not illuminate the background screen 114. For example, the shield 136 may be configured to block light that would otherwise illuminate the protective screen 110 or detrimentally impact image quality for reading the at least one identification tag 50. In certain embodiments, the entire bottom surface of the background screen 114 may be illuminated when the background screen 114 is configured for use as a light pipe.

Figure 12A:
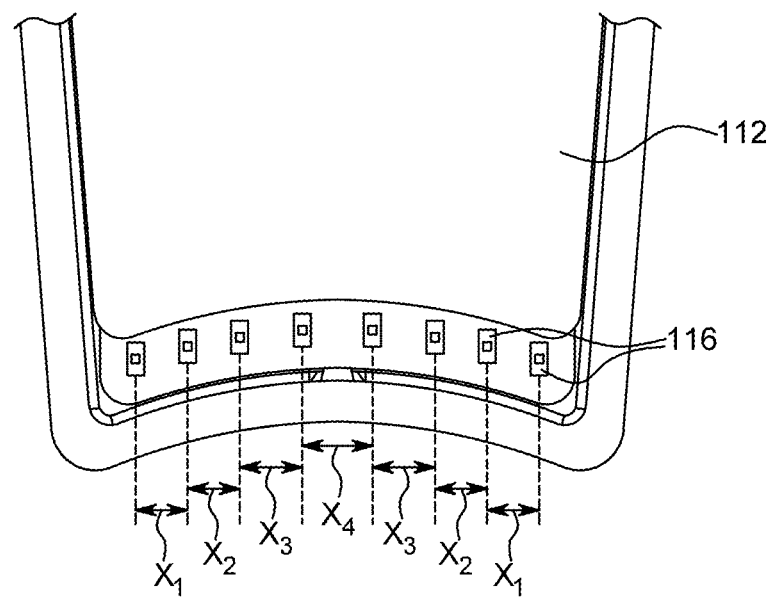
FIGS. 12A-12B are views of a lighting pattern projected by a lighting module of the syringe identification module shown in FIG. 7A.
Figure 12B:
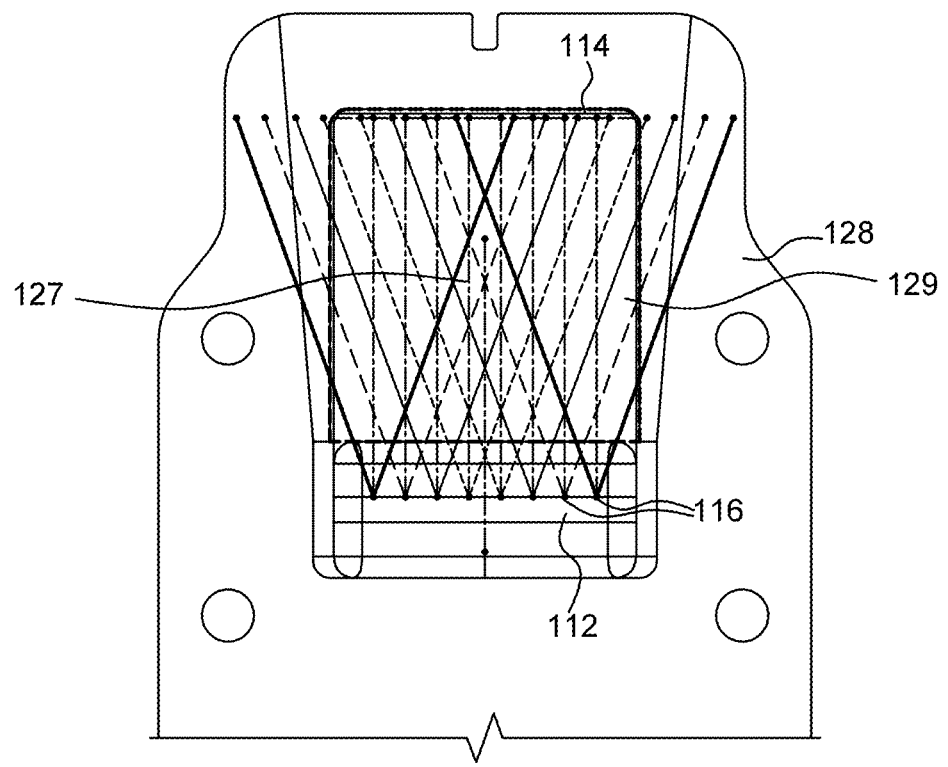

With reference to FIGS. 12A-12B, the plurality of light modules 116 may be spaced apart relative to one another with uniform or non-uniform spacing therebetween. In certain embodiments, the spacing $X_1$, $X_2$, $X_3$, $X_4$ between the light modules 116 and/or the light intensity of each of the light modules 116 may be varied to provide uniform illumination of the background screen 114. Uniform illumination may be important in various embodiments as the ability of the detector 104 to read the identification tag 50 may diminish when illumination level varies significantly between different portions of the identification tag 50. In some examples, the spacing of the light modules 116 may decrease in an outward direction from a center of the board of which the light modules 116 are positioned. The spacing near the edges of the light pipe is closer together because the edges of the light pipe are only illuminated by the LEDs near the edge, whereas portions near the center of the background screen 114 may be illuminated by light coming from several of the plurality of light modules 116. FIG. 12B illustrates overlap of lighted areas from the plurality of light modules 116 when the light modules 116 are evenly spaced resulting in greater light intensity near the central region 127 of the background screen 114 and lower light intensities near the lateral peripheral regions 129 of the background screen 114. In some examples, a textured surface at a proximal end of the background screen 114 immediately above the light modules 116 may be provided to disperse the light uniformly as it initially enters the background screen 114. In other embodiments, the peripheral regions 129 of the background screen 114 may include a larger concentration of embedded scattering elements or textured surfaces compared to the central region 127 of the background screen 114 to increase light scattering and therefor light intensities at the peripheral regions 129 to more closely match the light intensity of the central regions 127 of the background screen 114.

Alternative Examples

In some examples, the detector 104 may be a laser detector having a laser emitter and receiver. The detector 104 may be used without an illumination system 112 because the laser light emitted from the laser emitter illuminates the identification tag 50. One or more reflective elements 102 may be provided to deflect the laser rays such that the laser rays strike the at least one identification tag 50 at different angles. The laser receiver receives the reflected laser rays and reads identifying information associated with the identification tag 50 based upon the characteristics of the reflected laser rays. In some examples, the laser detector may be configured for reading 1-dimensional barcodes.

In other examples, rather than, or in addition to, illuminating the background screen 114 behind the at least one identification tag 50, the at least one identification tag 50 can be illuminated directly by the illumination system 112. For example, the illumination system 112 may illuminate the at least one identification tag 50 in a direction parallel with the optical path 109. Alternatively, or in addition, the illumination system 112 may illuminate the at least one identification tag 50 at an angle relative to the optical path 109. The illumination system 112 may illuminate the outer surface 21 and/or the inner surface 23 of the syringe 12.

In still other embodiments, the syringe sidewall 19 may act as an illuminated background screen, for example by acting as a light pipe having an illumination system 112 below the syringe sidewall 19. The illuminated syringe sidewall 19 may act as a background screen for at least one identification tag 50 located on the outer sidewall 21 of the syringe sidewall 19 or for at least one identification tag 50 laser etched into the interior of the syringe sidewall 19.

Method of Use

Having described the structure of the injector 10, the at least one identification tag 50, and the reader system 100, an embodiment of a method of reading at least one of the at least one identification tags 50 using the reader system 100 will now be described. When the syringe 12 is inserted into the syringe port 16, at least one of the at least one identification tags 50 is positioned in the space 130 between the protective screen 110 and the background screen 114 of the reader system 100. The injector's control mechanism 11 may send a command to the reader system 100 to initiate a scan or alternatively, the reader system 100 may automatically begin scanning upon insertion of the syringe 12. For example, the reader system 100 may turn on the illumination system 112 to illuminate the background screen 114 and, if necessary, focus the lens 106 on the at least one identification tag 50. The detector 104 is then activated to capture an image of the at least one identification tag 50 against the backdrop defined by the illuminated background screen 114. The captured image is then decoded using an algorithm programmed in the interface board 118 of the reader system 100 or within the injector software to extract information about at least one parameter of the syringe 12 and/or the fluid contained therein. Once the at least one identification tag 50 has been decoded, the reader system 100 may send the decoded information to the injector's control mechanism 11. The illumination system 112 may be turned off after the at least one identification tag 50 has been decoded.

Although the invention has been described in detail for the purpose of illustration based on what are currently considered to be the most practical and preferred examples, it is to be understood that such detail is solely for that purpose and that the invention is not limited to the disclosed examples, but, on the contrary, is intended to cover modifications and equivalent arrangements that are within the spirit and scope of the appended claims. For example, it is to be understood that the present invention contemplates that, to the extent possible, one or more features of any example can be combined with one or more features of any other example.

What is claimed is:

1. A method for reading information on at least one identification tag associated with a syringe, the method comprising:

locating at least one of the at least one identification tags associated with a sidewall of the syringe inserted between a background screen and a frame of a detector, such that the at least one of the at least one identification tags is positioned in an optical path between the detector and the background screen;

illuminating at least a portion of the background screen with an illumination system such that at least a portion of the at least one of the at least one identification tags is illuminated by the background screen;

detecting by the detector the at least a portion of the at least one of the at least one identification tags while it is illuminated by the background screen; and communicating with a control mechanism of a fluid injector at least one parameter from the at least one identification tag, wherein the background screen is spaced apart from the frame of the detector such that at least a portion of the syringe having the at least one identification tag is insertable in a space between the background screen and the frame.

2. The method of claim 1, further comprising decrypting at least one decryption code with unique identifying information associated with the at least one identification tag.

3. The method of claim 1, wherein the at least one parameter comprises a digital signature for the syringe, the method further comprising enabling operation of the fluid injector when the at least one identification tag associated with the syringe comprises a correct digital signature.

4. The method of claim 3, further comprising notifying a user that the syringe is not a correct syringe if the syringe does not comprise the correct digital signature.

5. The method of claim 3, further comprising disabling the fluid injector while the syringe is inserted in an injector port if the syringe does not comprise the correct digital signature.

6. The method of claim 1, wherein illuminating at least a portion of the background screen comprises illuminating a surface of at least the portion of the background screen.

7. The method of claim 6, wherein illuminating the surface comprises at least one of illuminating a painted surface of the background screen, illuminating a textured surface of the background screen, and illuminating a light pipe of the background screen.

8. The method of claim 1, wherein the detector is a digital camera and detecting at least a portion of the at least one identification tag comprises capturing a digital image of the at least one identification tag.

9. The method of claim 8, wherein capturing the digital image of the at least one identification tag comprises identifying and extracting information defining the at least one identification tag; and converting the information into usable data.

10. A method of reading with a reader system at least one of at least one identification tag associated with a syringe, the method comprising:

inserting the syringe into a syringe port associated with a fluid injector such that at least one of the at least one identification tags is positioned in a space between a protective screen of the reader system and an illuminated background screen of the reader system;

initiating a scan with the reader system of the at least one identification tag while it is illuminated by the illuminated background screen;

capturing an image of the at least one of the at least one identification tag against the illuminated background screen;

decoding the at least one identification tag;

extracting information about at least one parameter of at least one of the syringe and a medical fluid contained within the syringe; and sending the information to a control mechanism of the fluid injector.

11. The method of claim 10, further comprising turning on an illumination system to illuminate the illuminated background screen prior to initiating the scan with the reader system.

12. The method of claim 11, further comprising focusing a lens of the reader system onto the at least one of the at least one identification tag.

13. The method of claim 11, further comprising turning off the illumination system after decoding the at least one identification tag.

14. The method of claim 10, wherein decoding the at least one identification tag comprises using at least one algorithm programmed in the reader system or in injector software.

15. The method of claim 11, wherein turning on the illumination system comprises illuminating at least a portion of a surface of the illuminated background screen.

16. The method of claim 10, wherein the at least one parameter comprises a digital signature for the syringe, the method further comprising enabling operation of the fluid injector when the at least one identification tag associated with the syringe comprises a correct digital signature.

17. The method of claim 16, further comprising notifying a user that the syringe is not a correct syringe if the syringe does not comprise the correct digital signature.

18. The method of claim 16, further comprising disabling the fluid injector while the syringe is inserted in the syringe port if the syringe does not comprise the correct digital signature.

19. The method of claim 10, wherein capturing an image of the at least one of the at least one identification tag against the illuminated background screen comprises capturing a digital image of the at least one identification tag.

* * * * *

UNITED STATES PATENT AND TRADEMARK OFFICE
CERTIFICATE OF CORRECTION

| | |
|---|---|
| PATENT NO. | : 11,630,965 B2 |
| APPLICATION NO. | : 17/226639 |
| DATED | : April 18, 2023 |
| INVENTOR(S) | : Capone et al. |

It is certified that error appears in the above-identified patent and that said Letters Patent is hereby corrected as shown below:

In the Specification

In Column 1, Line 7, delete "2019," and insert -- 2019, now Pat. No. 10,977,463, --, therefor.

In Column 1, Line 40, delete "(Q-R)" and insert -- (QR) --, therefor.

In Column 1, Line 57, delete "demand There" and insert -- demand. There --, therefor.

In Column 8, Line 43, delete "Q-R" and insert -- QR --, therefor.

In Column 15, Line 62, delete "background scree" and insert -- background screen --, therefor.

In Column 16, Line 1, delete "and at" and insert -- an at --, therefor.

Signed and Sealed this
Eighteenth Day of July, 2023

Katherine Kelly Vidal
*Director of the United States Patent and Trademark Office*